(12) United States Patent
Liu et al.

(10) Patent No.: US 12,144,670 B2
(45) Date of Patent: *Nov. 19, 2024

(54) ARTIFICIAL INTELLIGENCE TRAINING WITH MULTIPLE PULSED X-RAY SOURCE-IN-MOTION TOMOSYNTHESIS IMAGING SYSTEM

(71) Applicants: Jianqiang Liu, Campbell, CA (US);
Manat Maolinbay, Gilroy, CA (US);
Chwen-yuan Ku, San Jose, CA (US);
Linbo Yang, Pleasanton, CA (US)

(72) Inventors: Jianqiang Liu, Campbell, CA (US);
Manat Maolinbay, Gilroy, CA (US);
Chwen-yuan Ku, San Jose, CA (US);
Linbo Yang, Pleasanton, CA (US)

(73) Assignee: AIXSCAN Inc., Sunnyvale, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 17/683,544

(22) Filed: Mar. 1, 2022

(65) Prior Publication Data
US 2022/0313176 A1 Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2024.01)
*A61B 6/02* (2006.01)
(Continued)

(52) U.S. Cl.
CPC ............. *A61B 6/541* (2013.01); *A61B 6/025* (2013.01); *A61B 6/032* (2013.01); *A61B 6/035* (2013.01);
(Continued)

(58) Field of Classification Search
CPC ......... A61B 6/467; A61B 6/08; A61B 6/4405; A61B 6/54; A61B 6/032; A61B 6/4441;
(Continued)

(56) References Cited

U.S. PATENT DOCUMENTS 4,716,581 A * 12/1987 Barud ............... A61B 6/4441
378/197
5,550,889 A * 8/1996 Gard ................. H01J 35/153
378/121
(Continued)

*Primary Examiner* — Irakli Kiknadze
(74) *Attorney, Agent, or Firm* — PatentPC; Bao Tran

(57) ABSTRACT

Disclosed are image recognition Artificial Intelligence (AI) training methods for multiple pulsed X-ray source-in-motion tomosynthesis imaging system. Image recognition AI training can be performed three ways: first, using existing acquired chest CT data set with known nodules to generate synthetic tomosynthesis Images, no X-ray radiation applied; second, taking X-ray raw images with anthropomorphic chest phantoms with simulated lung nodules, applying X-ray beam on phantom only; third, acquiring X-ray images using multiple pulsed source-in-motion tomosynthesis images from real patients with real known nodules and without nodules. An X-ray image recognition training network that is configured to receive X-ray training images, automatically determine whether the received images indicate a nodule or lesion condition. After training, image knowledge is updated and stored at knowledge database.

8 Claims, 7 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| *A61B 6/03* | (2006.01) | |
| *A61B 6/04* | (2006.01) | |
| *A61B 6/06* | (2006.01) | |
| *A61B 6/08* | (2006.01) | |
| *A61B 6/40* | (2024.01) | |
| *A61B 6/42* | (2024.01) | |
| *A61B 6/46* | (2024.01) | |
| *A61B 6/58* | (2024.01) | |
| *G01N 23/044* | (2018.01) | |
| *G01N 23/083* | (2018.01) | |
| *G01N 23/18* | (2018.01) | |
| *G06T 7/00* | (2017.01) | |
| *G06T 7/11* | (2017.01) | |
| *G06T 11/00* | (2006.01) | |
| *G06T 17/00* | (2006.01) | |
| *G06V 10/25* | (2022.01) | |
| *G06V 10/62* | (2022.01) | |
| *G16H 10/60* | (2018.01) | |
| *G16H 30/20* | (2018.01) | |
| *G16H 50/20* | (2018.01) | |
| *A61B 6/50* | (2024.01) | |

(52) U.S. Cl.
CPC ............ *A61B 6/0407* (2013.01); *A61B 6/06* (2013.01); *A61B 6/08* (2013.01); *A61B 6/4007* (2013.01); *A61B 6/4014* (2013.01); *A61B 6/4021* (2013.01); *A61B 6/405* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(58) Field of Classification Search
CPC ... A61B 6/4476; A61B 6/0407; A61B 6/4283; A61B 6/035; A61B 6/06; A61B 6/541; A61B 6/583; A61B 6/405; A61B 6/4014; A61B 6/4452; A61B 6/4482; A61B 6/542; A61B 6/025; A61B 6/4208; A61B 6/4007; A61B 6/4021; A61B 6/482; A61B 6/56; A61B 6/4275; A61B 6/502; A61B 6/5211; G06T 7/11; G06T 7/0012; G06T 17/00; G06T 11/003; G06T 11/005; G06T 11/006; G06T 7/0016; G06T 2207/10081; G06T 2210/41; G06T 2207/30064; G06T 2207/20081; G06T 2207/30096; G06T 2211/412; G06T 2207/10076; G06T 2211/436; G06T 2200/24; G06T 2207/30168; G06T 2207/20084; G16H 50/20; G16H 10/60; G16H 30/20; G16H 40/63; G06V 10/12; G06V 10/62; G06V 10/25; G06V 2201/032; G06V 2201/03; G01N 23/18; G01N 23/083; G01N 23/044; G01N 2223/401
USPC .................. 378/4, 22, 62, 18, 193, 196, 197
See application file for complete search history.

(56) References Cited

U.S. PATENT DOCUMENTS

| | | | | |
|---|---|---|---|---|
| 8,094,773 | B2* | 1/2012 | Boese | A61B 6/025 378/4 |
| 8,559,591 | B2* | 10/2013 | Boese | A61B 6/4014 378/9 |
| 11,992,357 | B2* | 5/2024 | Liu | G01N 23/044 |
| 2004/0109529 | A1* | 6/2004 | Eberhard | A61B 6/4028 378/23 |
| 2008/0285711 | A1* | 11/2008 | Avinash | A61B 6/025 378/22 |
| 2010/0091940 | A1* | 4/2010 | Ludwig | A61B 6/4028 378/22 |
| 2012/0008735 | A1* | 1/2012 | Maurer | A61B 6/488 378/5 |
| 2012/0189094 | A1* | 7/2012 | Neushul | A61B 6/035 378/19 |
| 2012/0195403 | A1* | 8/2012 | Vedantham | A61B 6/022 378/62 |
| 2012/0300901 | A1* | 11/2012 | Lewalter | H01J 35/13 378/126 |
| 2015/0043712 | A1* | 2/2015 | Wang | A61B 6/4021 378/42 |
| 2015/0320371 | A1* | 11/2015 | Heath | A61B 6/542 378/21 |
| 2018/0263578 | A1* | 9/2018 | Abramovich | A61B 6/4452 |
| 2018/0298970 | A1* | 10/2018 | Daugirdas | A61B 6/4476 |
| 2019/0126070 | A1* | 5/2019 | Hsieh | A61B 6/461 |
| 2019/0175131 | A1* | 6/2019 | Duewer | A61B 6/025 |
| 2020/0305809 | A1* | 10/2020 | Schwoebel | H01J 35/147 |
| 2020/0352530 | A1* | 11/2020 | Inglese | A61B 6/08 |
| 2021/0093275 | A1* | 4/2021 | Hoernig | A61B 6/5223 |
| 2021/0177371 | A1* | 6/2021 | Wang | A61B 90/39 |
| 2022/0142591 | A1* | 5/2022 | Zhou | A61B 6/032 |
| 2022/0319007 | A1* | 10/2022 | Liu | A61B 6/0407 |

* cited by examiner

ARTIFICIAL INTELLIGENCE TRAINING WITH MULTIPLE PULSED X-RAY SOURCE-IN-MOTION TOMOSYNTHESIS IMAGING SYSTEM

The present invention claims priority to Provisional Application Serial Nos. 63182426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

The current invention generally relates to method and apparatus of artificial intelligence (AI) based diagnosis training with X-ray images, and, more particularly, to a method and apparatus of artificial intelligence (AI) based diagnosis training for lung, breast diseases or flaw identification of an object with multiple pulsed X-ray source-in-motion tomosynthesis imaging systems.

BACKGROUND

Tomosynthesis, also Digital Tomosynthesis (DTS), performs high-resolution limited-angle tomography at radiation dose levels comparable with projectional radiography. It has been studied for various clinical applications, including vascular imaging, dental imaging, orthopedic imaging, mammographic imaging, musculoskeletal imaging, and lung imaging. One advantage is that the DTS X-ray dose level is far less than CT imaging dose level. DTS is also much faster than CT and costs far less. Although it can run fast, it still relies primarily on humans for diagnostics purposes. Therefore, the operation overhead will add up to slow down the diagnostics process.

X-ray tomosynthesis imaging is typically performed in a clinical setting by trained X-ray experts. There are particular views of an organ or other tissue for diagnostic X-ray imaging that are clinically significant. Clinical standards may prescribe views that should be captured by the X-ray technician, depending on the diagnostic purpose. X-ray technicians generally require specialized training to operate X-ray imaging equipment properly and to recognize lung nodule or breast cancer from standard clinical view when a group of X-ray tomosynthesis image is acquired.

Nonetheless, X-ray tomosynthesis images captured by an X-ray technician are typically reviewed by a physician to determine whether the captured images sufficiently indicate a lung nodule condition or a breast cancer condition with the clinically standard views. While conventional X-ray imaging systems may be suitable for most patients in a hospital or similar clinical setting, such systems require significant training to operate. This would add to the overall cost of such X-ray imaging and further limits the availability to general patients, as only well-trained professionals can properly operate conventional X-ray imaging apparatus. As a result, conventional X-ray imaging system personnel training requires a significant amount of resources.

In order to perform fast lung cancer screening and breast cancer screening for everybody at low cost, it is therefore desirable to provide much improved systems and methods for diagnosing lung or breast conditions. Therefore, Artificial Intelligence (AI) based diagnosis technique is becoming necessary. Before Artificial Intelligence (AI) based diagnosis can be performed, Artificial Intelligence (AI) diagnosis training through machine learning is necessary in order to set up knowledge database.

CT imaging has been traditionally used as the primary source of 3D X-ray image data. CT images also offer accurate representation of patient geometry. Therefore, a synthetic tomosynthesis image can also be derived from an CT image for Artificial intelligence diagnosis training purpose. Using anthropomorphic chest phantoms with simulated lung nodules is also a good option to do Artificial intelligence diagnosis training. It might be also necessary to take a large amount of real human data in order to do machine learning.

Artificial intelligence approaches are characterized by using an X-ray image recognition software package to make diagnosis determinations about X-ray images captured with this kind of fast multiple X-ray source-in-motion tomosynthesis imaging system. The X-ray image recognition software package need huge computation power and usually runs at cloud AI training computing network. The X-ray tomosynthesis imaging system may also receive frequent monthly, weekly, or daily updates from the AI training networks thus receiving the most recently developed X-ray image knowledge stored in the AI training network with each update.

SUMMARY

Artificial Intelligence based training methods for diagnosis purpose are presented for multiple pulsed X-ray source-in-motion tomosynthesis Imaging systems. The training processes also performed at cloud computing using Artificial intelligence diagnosis training networks.

In one aspect, Artificial Intelligence based training is performed with existing CT data. The acquired CT 3D images are from real patients with real known nodules. Then, using geometry of tomosynthesis imaging systems, it is possible to generate synthetic tomosynthesis raw image data using CT forward project data just like that at X-ray flat panel detector. By applying backward projection, CT forward project data can be reconstructed into synthetic tomosynthesis image data just like what people see at clinically standard views. Using synthetic tomosynthesis image data with real annotated nodule, Artificial Intelligence based training then can be performed and knowledge data base can be updated. During this training process, there is a no X-ray beam involved. Advantage is that. Therefore, it is beneficial if a "pseudo tomosinthesis image" or a "synthetic image," such as a pseudo or synthetic tomosynthesis image could be derived from an acquired CT image. Specifically, a supervised learning algorithm uses a known set of input data and known responses or outputs to that data, and then trains a model to generate reasonable predictions for the response to new data. Advantages of the system may include one or more of the following. The system generates synthetic data that is realistic and checked to indicate lung nodule with clinically standard views for training neural networks and AI. The data can be used for a variety of purposes, including model validation and AI model training and data augmentation. The synthetic data can be created to meet certain needs or conditions not found in real data. This is useful in many cases. For example, privacy requirements in medical settings may limit data availability and how it can used.

Privacy rules and other regulations may place limitations on the use of real data. In other examples, for a product to be tested, data is required. However, such data is either not available or not yet available to testers. Machine learning algorithms require training data. This is especially true for radiologic or other medical uses as it can be costly to generate such data in real life. The ability to generate data that is identical to real medical data can be a limitless tool for creating scenarios for testing or development synthetic data can replicate the statistical properties found in real data and yet not revealing any real patient data. Data creation can simulate conditions not yet experienced: synthetic data is the only way to go when real data is not available. These benefits show that synthetic data creation and use will continue to rise as data becomes more complex and is more tightly protected.

In another aspect, Artificial Intelligence based training is performed with anthropomorphic chest phantoms with simulated lung nodules. During Artificial Intelligence training processes, X-ray tomosynthesis images are acquired by using anthropomorphic chest phantoms with simulated lung nodules at known location. By comparing phantoms images with nodules and without nodules, Artificial Intelligence based training then can be performed and knowledge data base can also be updated. During this training process, X-ray radiation is only on phantoms, not on real patients.

In another aspect, Artificial Intelligence training is performed with real patients with real lung nodule. Firstly, X-ray tomosynthesis images are acquired from real patients with real known nodules. Secondly, X-ray tomosynthesis images are acquired from real patients without real nodules. By comparing patient images with nodules and without nodules, Artificial Intelligence based training then can be performed and knowledge data base can also be updated. During this training process, X-ray radiation needs to be on patients.

The X-ray image recognition software package is configured to receive the X-ray image knowledge, receive the acquired X-ray images from the X-ray tomosynthesis imaging system, and based on the X-ray image knowledge, determines whether the received X-ray images reveal a lung nodule or breast cancer condition. The received X-ray images are transmitted to the X-ray image recognition training network to further train and develop updated X-ray image knowledge.

BRIEF DESCRIPTION

This application will become more fully understood from the following detailed description, taken in conjunction with the accompanying figures, wherein like reference numerals refer to like elements in which.

DETAILED DESCRIPTION

In the following paragraphs, the present invention will be described in detail by way of example with reference to the attached drawings. Throughout this description, the preferred embodiment and examples shown should be considered exemplars rather than limitations on the present invention. As used herein, the "present invention" refers to any one of the embodiments of the invention described herein and any equivalents. Furthermore, reference to various features of the "present invention" throughout this document does not mean that all claimed embodiments or methods must include the referenced features.

However, this invention may be embodied in many different forms and should not be construed as limited to the embodiments set forth herein. These embodiments are provided so that this disclosure will be thorough and complete and fully convey the invention's scope to those of ordinary skill in the art. Moreover, all statements herein reciting embodiments of the invention and specific examples thereof are intended to encompass structural and functional equivalents. Additionally, it is intended that such equivalents include both currently known equivalents and equivalents developed in the future (i.e., any elements developed that perform the same function, regardless of structure).

Figure 1:
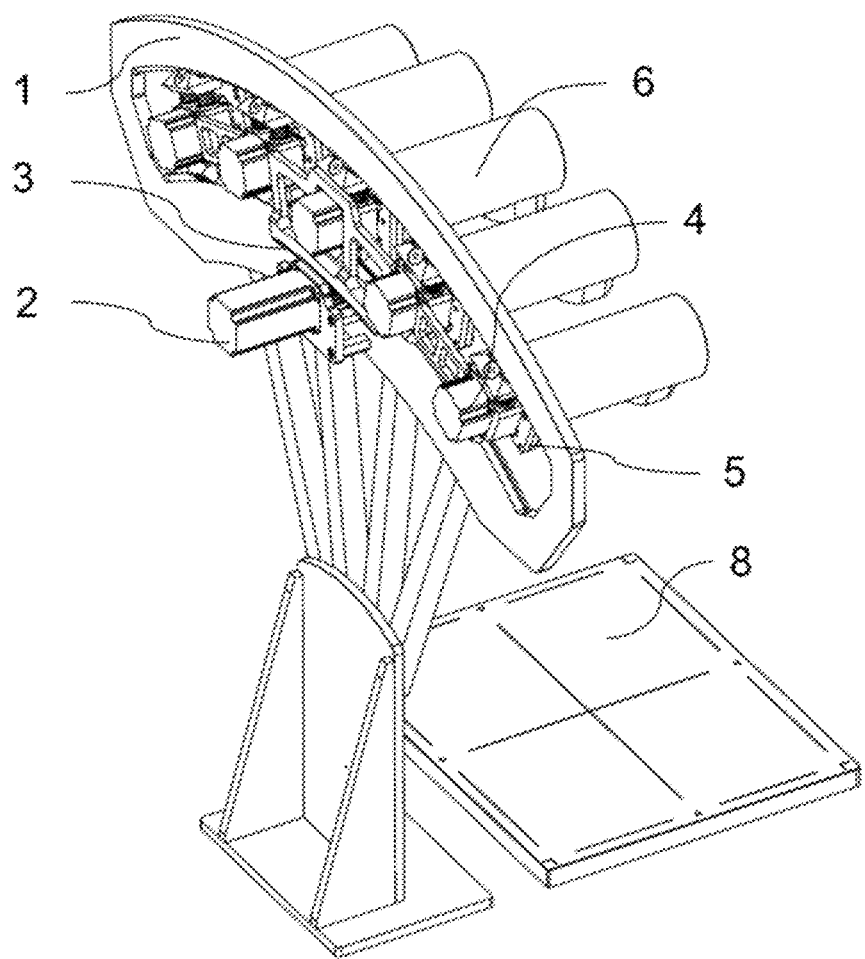
FIG. 1 illustrates an exemplary multiple pulsed X-ray source-in-motion tomosynthesis imaging system.

FIG. 1 shows an exemplary X-ray imaging system using multiple pulsed X-ray source-in-motion to perform high efficient and ultrafast 3D radiography. It is called multiple pulsed X-ray source-in-motion tomosynthesis imaging system 1. Multiple pulsed X-ray sources are mounted on a structure in motion to form an array of sources. The multiple X-ray source tube 6 move simultaneously relative to an object on a pre-defined arc track at a constant speed as a group. The group of tubes are on a primary motor stage 3 and the movement is controlled by a primary motor 2. Each X-ray source tube can also move rapidly around its static position at a small distance. Each tube is on a secondary motor stage 5 and small vibration movement is controlled by a secondary motor 4. When an X-ray source has a speed equal to group speed but with opposite moving direction, the X-ray source 6 and X-ray flat panel detector 8 are activated through an external exposure control unit to stay standstill momentarily. This configuration results in a much-reduced source travel distance for each X-ray source 6. The 3D scan can cover a much broader sweep angle in a much shorter time, and image analysis can also be done in real-time. This type of X-ray machine utilizes many more X-ray sources 6 than other types of X-ray image machines to achieve a much higher scan speed.

One embodiment of a tomosynthesis imaging system has four significant parts: digital radiography system, 3D slice projection equipment, multi pulsed source in motion control systems and image recognition software package. The 3D scanner uses an industrial computer for data processing, network devices for signal transfer, computers with sufficient storage for data analysis, and high-performance graphic cards to display the processed data. The imaging system can be connected to a hospital network and may transmit image files to the central hospital network. The system can transmit patient information and diagnosis result to the doctor's office. The system can reduce X-ray dose and speed up the diagnostic process through the use of multiple pulsed sources that can achieve seconds shot and thus reduces radiation dosage while decreasing scan time.

Figure 2:
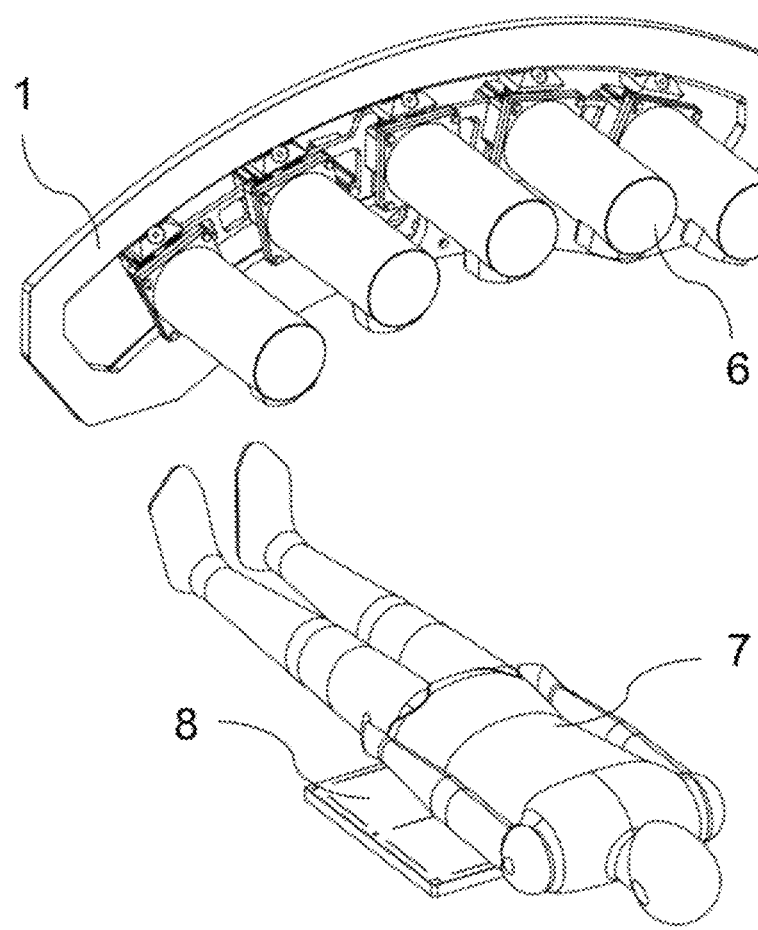
FIG. 2 shows an exemplary diagnostics scan of a patient or an object using an multiple pulsed X-ray source-in-motion tomosynthesis imaging system.

FIG. 2 shows a diagnostics scan of a patient or an object 7. The new X-ray imaging system uses multiple pulsed X-ray sources-in-motion to perform X-ray imaging primarily for lung imaging or breast mammography. This system does not need to take the image of arms. It can easily take up to 120 degrees or more to scan in a few seconds. In FIG. 2, there are multiple X-ray sources 6, a patient 7 is placed in front of an X-ray flat panel detector 8. Multiple X-ray sources 6 is rotated around the body area or organ being imaged. For example, a lung of a patient. X-ray imaging detector 8 is designed to revolve around the subject's body to capture multiple source images in multiple source positions from each source position at different angles and store these into the computer storage as multiple source raw images. From multiple source positions, the images are further processed to form more information about nodules. For example, it can be combined with multi-view detectors and dose-reducing detectors. Further processing may involve computer vision such as registration of data sets, segmentation, background modeling, object classification, 3D reconstruction, visualization, n and so on. Computer vision will make these diagnostics more automatic and cost-effective. Electronic X-ray imaging detector is usually made up of rows of solid-state image sensors sometimes equipped with additional filters also rows of ionization chambers and in some cases even scintillation materials. It will have rows of photodiodes sometimes made of avalanche photodiodes or rows of CCD CMOS sensors which will convert X-ray photons to electrons which will then be converted to digital values that correspond to the intensity of the radiation received by the sensor all depending on the technology used.

The patient 7 in a diagnostic radiology procedure room lies on an examination table. The patient is undergoing imaging by a multiple pulsed X-ray source-in-motion tomosynthesis imaging system 1. The tomosynthesis imaging system may include external supports that position the tomosynthesis imaging system over the patient and support a gantry.

Figure 3:
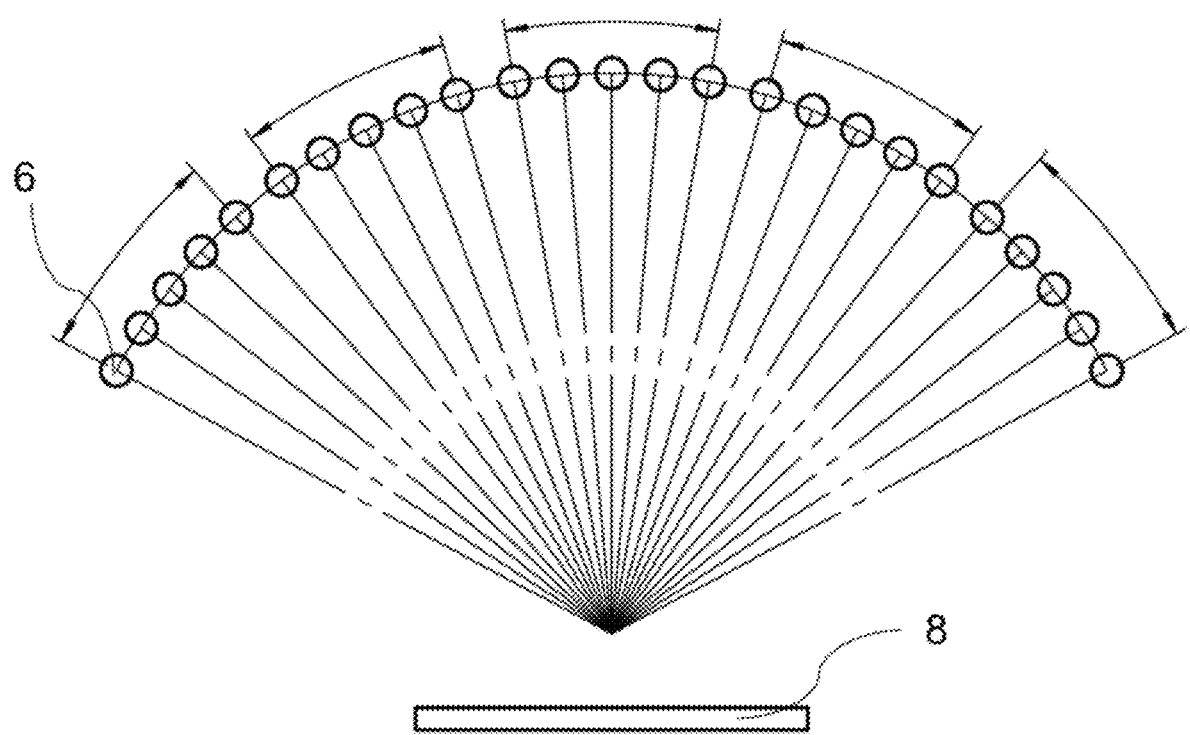
FIG. 3 shows an exemplary tomosynthesis imaging system sweep scan geometry with five X-ray source tubes.

FIG. 3 shows an exemplary sweep scan geometry with five X-ray source tubes 6. It illustrates an exemplary five-X-ray-source-tube configuration that takes 25 sets of projection data by each traveling only one-fifth of the total distance. In this implementation, there are five X-ray source tubes 6 working in parallel and the five X-ray source tubes 6 perform 25 total X-ray exposures at different angle positions. But each secondary motor stage 5 only needs to travel one-fifth of the total covered angle. Therefore, with multiple X-ray source tubes 6 working in parallel, a large amount of projection data can be acquired at a fraction of amount of time. X-ray flat panel detector 8 is served as an X-ray receiver. Lung digital tomosynthesis enables acquisition of a set of tomographic image data from the entire field of view in a short exposure time. Electronic signals always go faster than mechanical motion so that bottleneck is always from mechanical side.

Figure 4:
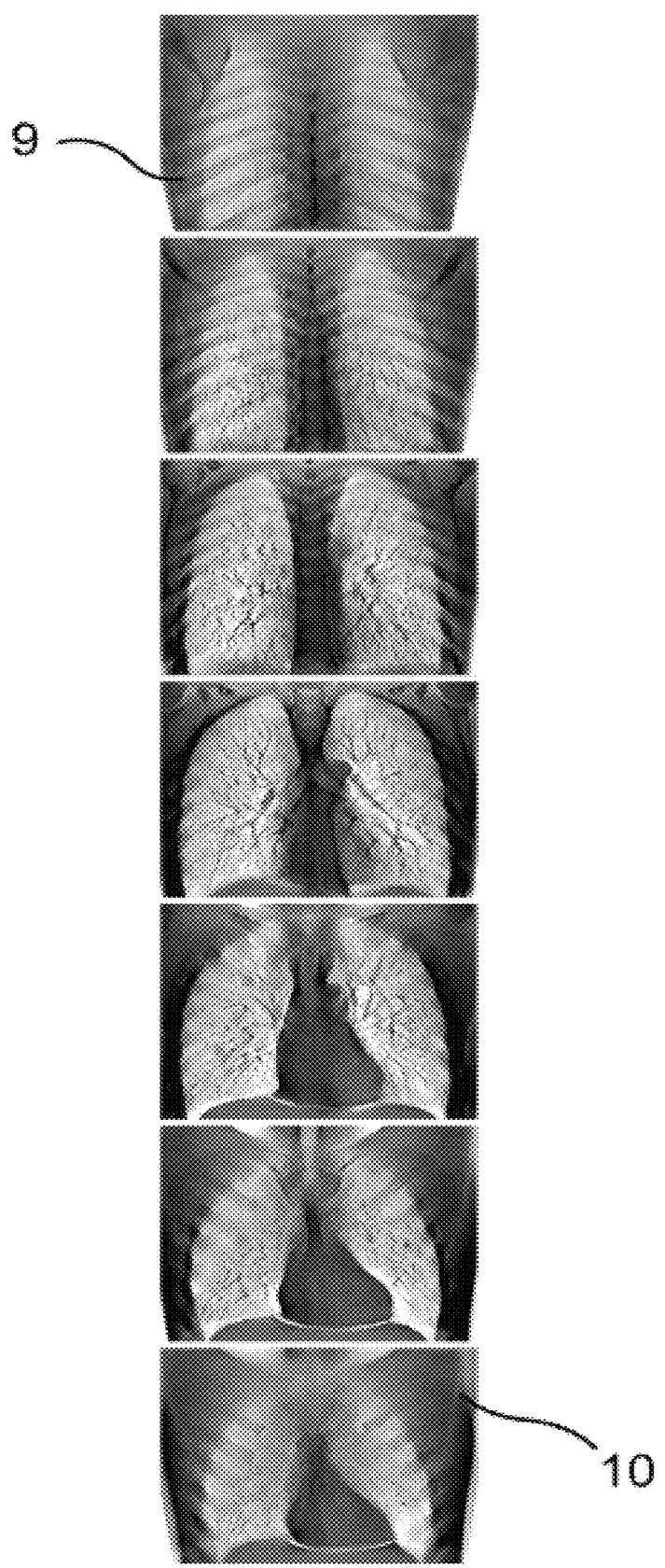
FIG. 4 shows a collection of acquired X-ray images from multiple pulsed source-in-motion tomosynthesis imaging system using anthropomorphic chest phantoms with simulated lung nodules.

FIG. 4 shows acquired X-ray images from multiple pulsed X-ray source-in-motion tomosynthesis imaging system 1 using anthropomorphic chest phantoms with simulated lung nodules. The display of the X-ray tomosynthesis images are with clinically standard view or clinically desired view. This kind of display of images are accepted by most of radiologists and doctors. The acquired X-ray tomosynthesis images in the beginning of a scan 9 are at the top and acquired X-ray tomosynthesis images in the end of a scan 10 are at the bottom. It reveals that tomosynthesis lung images are actually 3D images with limited angles of view. In lung tomosynthesis, the x-ray tubes moves in an arc over the lung capturing multiple images of lung from different angles. These digital images are then reconstructed or "synthesized" into a set of three-dimensional images by a computer. Lung digital tomosynthesis is a limited angle image tomography, which improves the visibility of anatomy compared with radiographic imaging. Due to the limited acquisition angle of Lung digital tomosynthesis, it has the potential to significantly increase the temporal resolution of patient surveillance at the cost of reduced resolution in one direction. Lung digital tomosynthesis is several times more effective in identifying pulmonary nodules compared to conventional radiography and at lower doses and cost compared with routine chest computed tomography (CT) examinations. The multiple pulsed X-ray source-in-motion tomosynthesis imaging system 1 is able to produce large amount of high quality 3D X-ray imaging data in very short amount of time. Although those X-ray images can be viewed and examined by radiologists one-by-one, this machine is really designed for Artificial Intelligence (AI) to read and make a quick diagnosis decision.

X-ray tomosynthesis imaging system typically produces a set of three dimensional 3D X-ray images each X-ray image representing a thin slice of an organ or other tissue of a patient. X-ray tomosynthesis imaging system often acquires additional views including anterior, posterior, and lateral images. The set of 3D X-ray images may be displayed in order or combined into a single composite view as the viewing direction rotates around the patient. For example, lung cancer screening requires capturing X-ray images that show adequate visualization of at least one complete lobe of a patient's lung. The determination of clinical acceptability can vary—different systems exist, whether it is based on anatomical structure or scanning the image in a pattern.

The X-ray detector 8 has an array of X-ray sensitive elements that sense X-rays and provide information that is indicative of a location of the region of interest. The information may be digitized or otherwise processed to determine this location. A storage device stores data representative of images generated by a tomosynthesis imaging system. This stored data includes image information acquired by tomosynthesis imaging and corresponding slice location data that indicates the position of each acquired image relative to other images in the dataset. These data are used for training artificial intelligence algorithms such as neural networks. The artificial intelligence system consists of at least one processing element coupled to a memory. The processing element may be configured to receive input data from at least one user through a user interface. Input data may include medical X-ray images and or images that are representative of the nodule or tumor detected in the patient's lung or chest. In addition the processing element may be configured to perform the functions described herein. For example, it may be configured to compare an image to reference images or predetermined diagnostic criteria. A suitable processing element may be provided by a general purpose computer executing software, hardware or a combination thereof.

To increase speed and accuracy in identifying potential medical issues from a patient scan, artificial intelligence (AI) is applied. To improve performance and reduce cost, the preferred embodiment applies AI as a diagnostics tool to perform data acquisition and make diagnostics decisions. AI must be trained first before AI can be used as a decision-maker in multiple pulsed source-in-motion tomosynthesis imaging systems. An AI program has to be trained first. AI software uses virtual images created by reconstruction from raw data from tomosynthesis imaging system or anthropomorphic chest phantoms with stimulated lung nodules, including GroundGlass Opacity (GGO) nodules and Chronic Obstructive Pulmonary Disease (COPD) nodules, to get training data sets. Anthropomorphic phantoms are made of materials with similar tissue characteristics to normal biological organisms. Due to their limited availability and likeness to actual patients, anthropomorphic phantoms can be used for various tasks.

Artificial intelligence (AI) or machine learning model is a mathematical algorithm that is trained to come to the same result or prediction that a human expert would when provided the same information. Deep learning neural networks, or artificial neural networks, attempts to mimic the human brain through a combination of data inputs, weights, and bias. These elements work together to accurately recognize, classify, and describe objects within the data. Deep learning is a subset of machine learning, which is itself a subset of artificial intelligence (AI). Deep neural network represents the type of machine learning when the system uses many layers of nodes to derive high-level functions from input information. The "deep" in deep learning refers to the many layers the neural network accumulates over time, with performance improving as the network gets deeper. A Convolutional Neural Network is a deep learning algorithm which can take in an input X-ray tomosynthesis image, assign importance by learnable weights and biases to various aspects or objects in the X-ray tomosynthesis image and be able to differentiate one from the other. Convolutional Neural Networks (CNNs) are one of the most popular neural network architectures. They are extremely useful at X-ray tomosynthesis image processing. Machine learning is about computers being able to think and act with less human intervention; deep learning is about computers learning to think using structures modeled on the human brain. Deep learning can analyze X-ray tomosynthesis mages in ways machine learning can't easily do.

With the trained AI software that can process X-ray tomosynthesis images in order to detect cancerous lesions or any other kind of lesions, radiologists reviews of X-ray scan images can be reduced significantly to reduce doctor workload. Tomosynthesis imaging with AI recognition of results will save time and cost especially for those patients who are too old or sick to undergo CT scanning. To train the AI system, three methods are disclosed in FIGS. 5-7 as detailed below.

Figure 5:
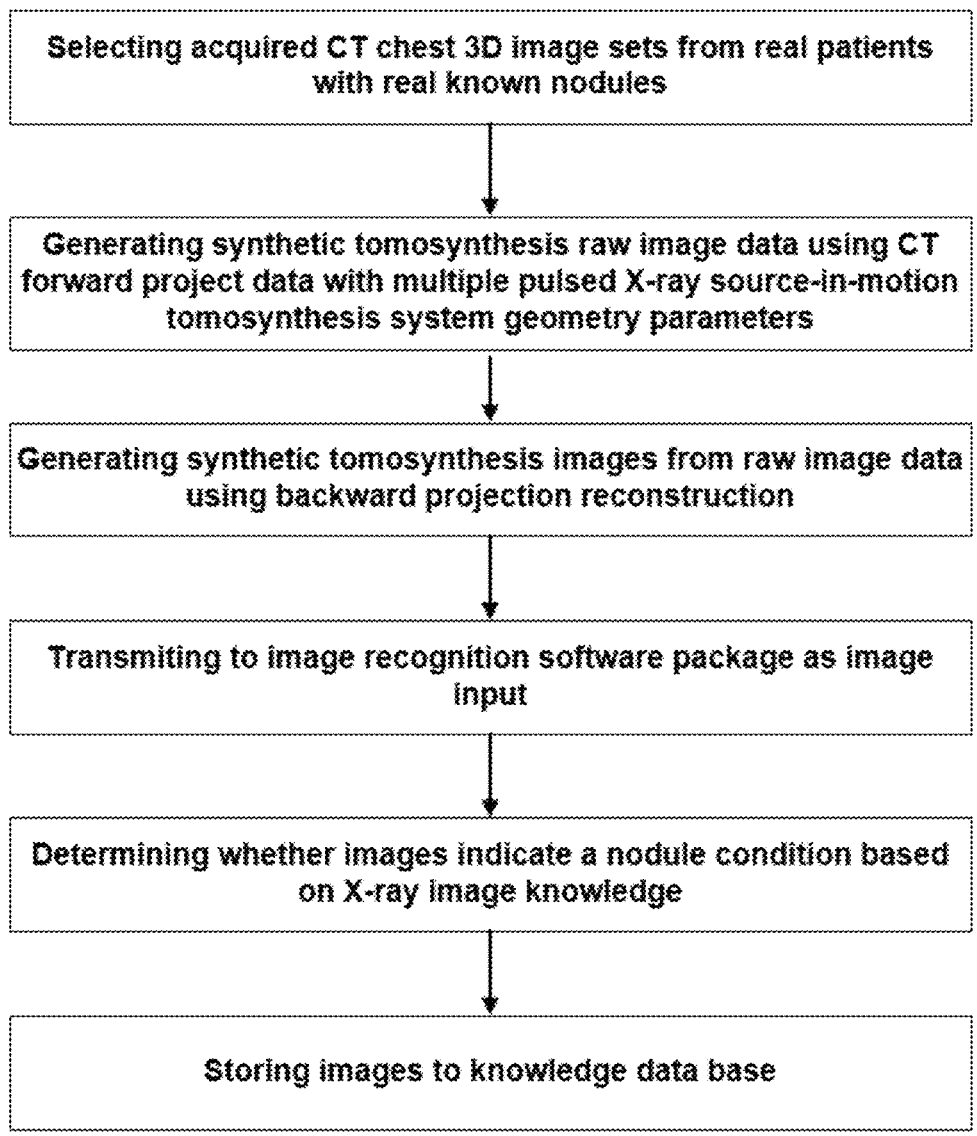
FIG. 5 shows an AI training flow chart at a typical multiple pulsed X-ray source-in-motion tomosynthesis imaging scan using synthetic tomosynthesis images generated from an set of CT image.

As method ONE of AI training, FIG. 5 shows an AI training flow chart at a typical multiple pulsed X-ray source-in-motion tomosynthesis imaging scan using synthetic tomosynthesis image generated from an CT image. CT can get much more comprehensive data with high expense and high X-ray dose. CT annotated forward project would create a virtual phantom. For Artificial Intelligence (AI) image recognition training, if there is no actual patient raw data available, it is possible to use annotated CT lung images with known nodules. Forward project of CT lung images can act as virtual object phantom for the tomosynthesis imaging system geometry. The forward project data is equivilant to raw data at X-ray detector. Then, from forward project data it is possible to do the backward projection to produce 3D tomosynthesis imaging as training data set with clinically standard view.

The geometry of a typical multiple pulsed X-ray source-in-motion tomosynthesis imaging system includes X-ray source to detector distance, X-ray source to object distance, X-ray scan sweeping angle, X-ray flat panel detector size and incremental angles etc. and the cone-beam projection geometry can be identified in FIG. 1. The forward projection can be performed mathematically using those geometry parameters.

Generating tomosynthesis images using CT forward project data and backward projection is based on the fact that similar tissue attenuation can be used to get tomosynthesis images. In one method, the process uses forward project with thickness correction for creating CT scan image sets and back projection reconstruction to reconstruct those data sets into a tomosynthesis image format. One advantage of this method is that the tomosynthesis images are created with accurate knowledge of X-ray doses due to the high accuracy of forward projection imaging and another advantage is that the speed of tomosynthesis imaging is relatively fast. The training data set is sent to Intelligence (AI) image recognition training network as input. The training output is then stored as image knowledge database. In method one, there are no actual X-ray beam activities at the tomosynthesis imaging system.

The process of creating virtual patients from a CT image data set is detailed next. Registration of CT images, and 3D phantoms CT images can be registered to the anthropomorphic phantoms using point to point matching based on a small number of anatomical features in one embodiment. For example, edges on the phantom to help register the CT images to the reference volume typically four or five points per patient would be sufficient for registration. However more points can be used for improved accuracy. This process should also work with deformable templates instead of fixed landmarks. The output of this step will be a group of patient-specific target volumes corresponding to each patient's CT image data set. There will be a forward projection data set as well as a backward projection data set for each target volume. These target volumes are essentially stand-ins for each patient's CT image data set representing the same geometry but with the materials characterized by the different levels of voxel density that result from the CT scanning process. Material values may be estimated for all the voxels in the target volumes. It may be desirable to smoothen the target volumes to obtain accurate estimates of the material values at the interface between bone and soft tissue.

Figure 6:
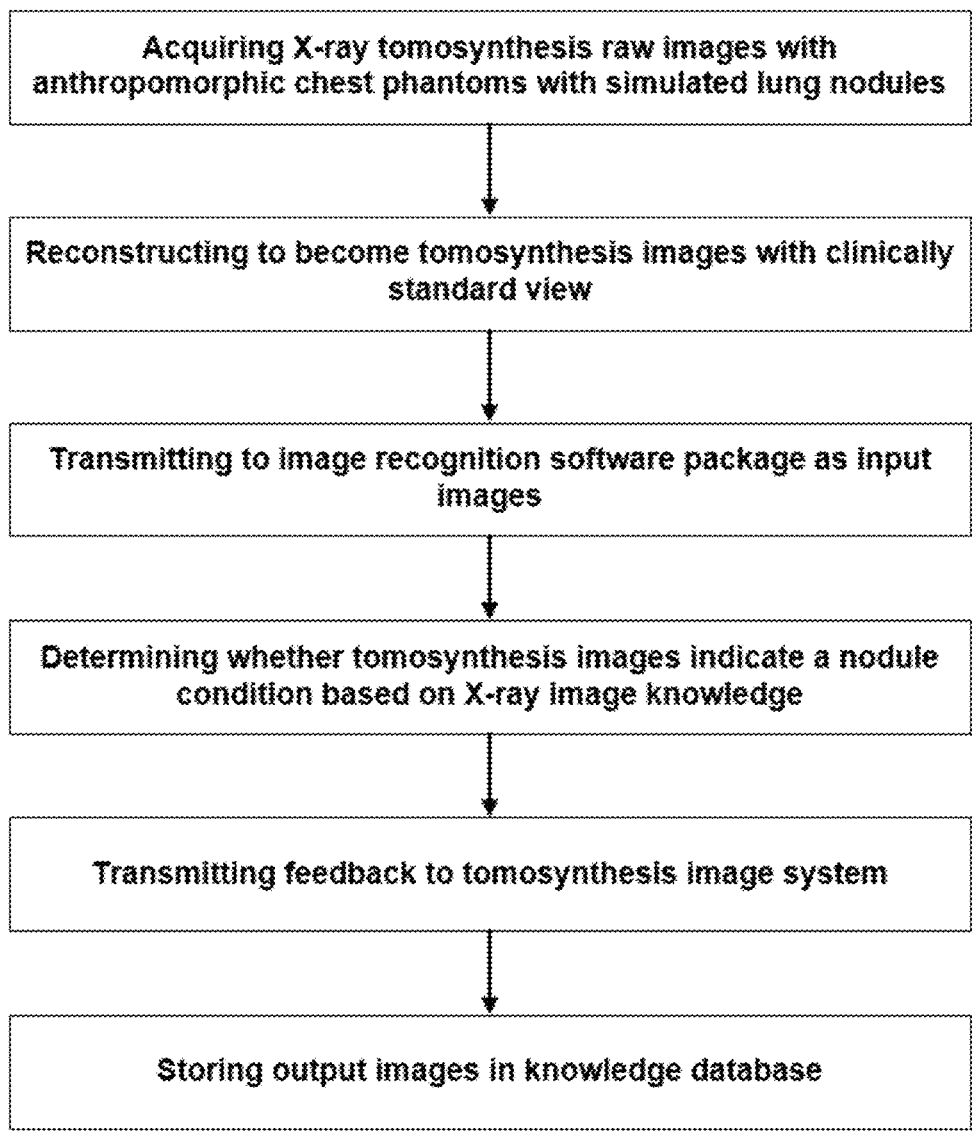
FIG. 6 shows another alternative AI training flow chart at a typical multiple pulsed X-ray source-in-motion tomosynthesis imaging system using anthropomorphic chest phantoms with simulated lung nodules.

As method TWO of AI training, FIG. 6 shows another alternative AI training flow chart at a typical multiple pulsed X-ray source-in-motion tomosynthesis imaging system using anthropomorphic chest phantoms with simulated lung nodules. The lung nodules include GroundGlass Opacity (GGO) nodules and Chronic Obstructive Pulmonary Disease (COPD) nodules to get training data sets. Anthropomorphic phantoms are made of materials with similar tissue characteristics to normal biological organisms. Due to their limited availability and likeness to real patients, anthropomorphic phantoms can be used for a variety of tasks. The GGO nodules and COPD nodules is the main task to get image recognition software as well as a correct diagnosis. Chest phantoms can be in a standard or prescribed view such as the anteroposterior chest view. Using these simulated nodules, the system can build several database images for tomosynthesis imaging system to get different training data sets with different number of nodules and different locations of nodules for each training data set. Using maximum likelihood estimate (MLE), the corresponding number of normal structures that will lead to the acquired image is determined. MLE is used to identify statistically likely parameters for the acquired X-ray image by making a mathematical model of the acquisition process. Determining what statistical distribution it would most likely fall into and evaluating the likelihood of the image given the assumed model, this knowledge base can then be fed back into the system for future interpretation and decision making of X-ray images. Such a trained artificial intelligence learning network may then operate independently in conjunction with a radiologist or in any additional capacity desired to prevent misdiagnosis. The presented method requires pre-specified criteria be met before clinical decisions are made on images generated by the presented methods. The anthropomorphic chest phantom training data set is sent to Intelligence (AI) image recognition training network as input. Phantom patient data has to be realistically generated for training the deep learning system. The training output is then stored as image knowledge database. In method two, X-ray beam activities only happen at the phantom, not at people. CT results and phantom results can be compared to improve machine learning.

Figure 7:
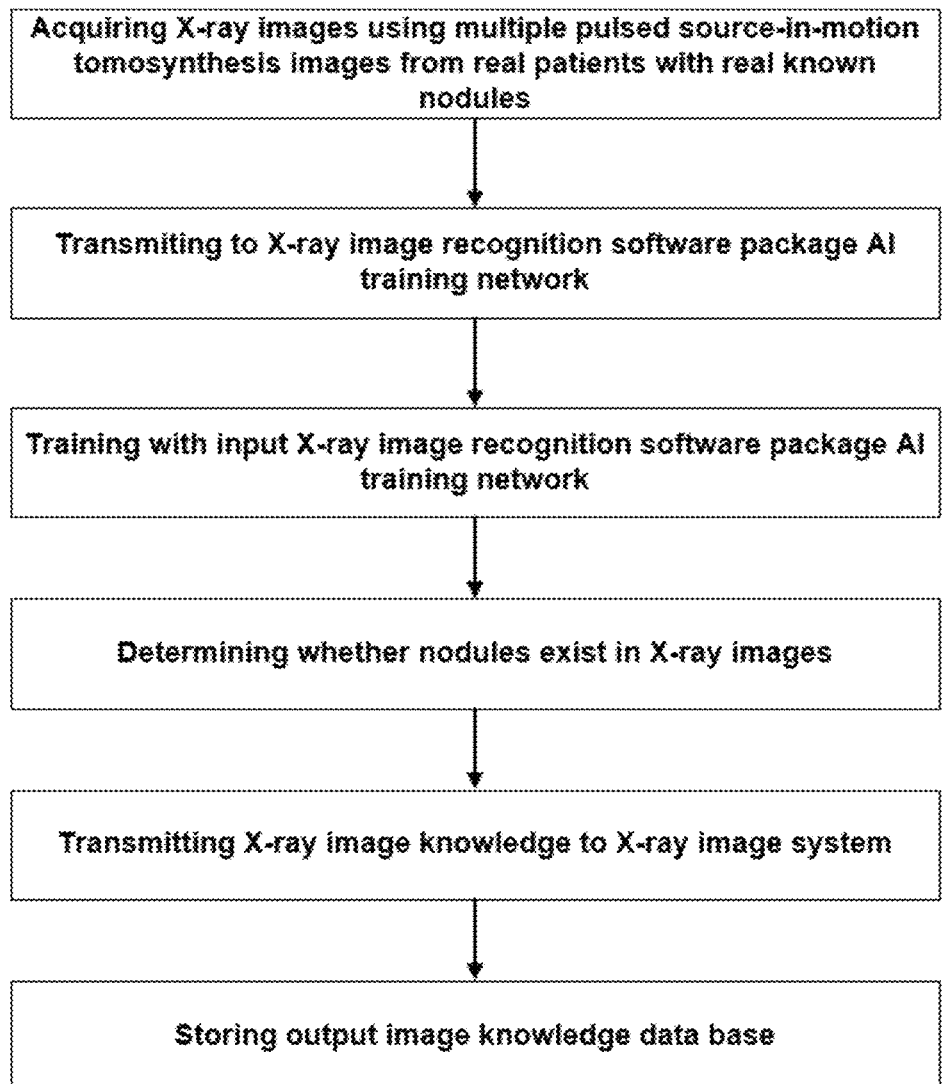
FIG. 7 shows another alternative AI training flow chart at a typical multiple pulsed X-ray source-in-motion tomosynthesis imaging system using actual patients.

As method THREE of AI training, FIG. 7 shows another alternative AI training flow chart at a typical multiple pulsed X-ray source-in-motion tomosynthesis imaging system 1 using actual patients. Using actual patients to take training data sets would need quite some efforts. It is desirable if there are, say need 1000 patients, 500 patients with known nodules, and 500 patients without nodules. The challenge is that there may not have enough patients. The training data set is sent to Intelligence (AI) image recognition training network as input. The training output is then stored as image knowledge database. In method THREE, X-ray beam activities will actually happen at at people. Typically the acquiring of X-ray tomosynthesis images from real patients without nodules can take quite some effort and a lot of resources. These data will be further processed into training data sets by segmenting them to several groups such as abcdefg and so on. Then each group would have forward projection and backward projection segmented image abcdefg and so on. After this process, they can be labeled abcdefg and so on. After labeling the images, they are divided into two groups A and B which contains both ground glass opacity GGO nodules and chronic obstructive pulmonary disease COPD nodules and can be used as training data set for X-ray image recognition software and also to develop X-ray image knowledge for AI system. The phantom results and real patient results can be compared. Acquiring a limited number of training data sets such as to improve the accuracy of automated nodule detection and false negative rate in subsequent clinical applications. Also we train the deep learning model with more available clinical images which could give better performance. Therefore there are several advantages in this invention such as eliminate the cost of the man hours to annotate each raw CT image for forward project training from simulated patients which could give much higher resolution and simulate what will happen in clinical situation. For example, for heart CT cases we have only images with a few hours work time using heart CT cases would more hours to annotate while with simulated patient you only need a few minutes and no limitation on how many times it should be done using deep learning networks to achieve better result by training from more clinical cases.

An external exposure control unit may be configured to receive data from the training network and adjust the radiation dose to a level that provides optimal development of the AI-based X-ray image recognition training network. The external exposure control unit may be any unit or combination of units that are capable of performing the desired adjustment of the radiation dose. As an example, the external exposure control unit may be an integral part of the imaging system or it may be a separate unit not shown connected to the imaging system. By way of a wired or wireless connection, an embodiment of the multiple pulsed source-in-motion tomosynthesis imaging system includes an artificial intelligence based X-ray image recognition training network that is configured to receive X-ray training images and to develop X-ray image knowledge base. On the received X-ray training images, an X-ray imaging system acquires X-ray images from a patient and the tomosynthesis imaging system includes an X-ray image recognition software package. The X-ray image recognition software package is configured to receive the X-ray image knowledge and receive the acquired X-ray images from the X-ray imaging system. Based on the X-ray image knowledge it determines whether the clinically standard views indicate normal function. The received X-ray images are transmitted to the X-ray image recognition training network for further training and development of updated X-ray image knowledge base.

A single tomosynthesis imaging system using one or more methods can receive input on the developed X-ray image knowledge. The input information can include any information about the knowledge such as but not limited to training knowledge obtained from images that have been analyzed by the training network. In this way, an X-ray image recognition software package in cooperation with the acquired X-ray image knowledge may determine whether images with the clinically standard views indicate lung normal healthy condition. In some embodiments, an X-ray data information system includes an X-ray image recognition training network that is configured to receive X-ray training images and to develop X-ray image knowledge based on the received X-ray training images.

The tomosynthesis imaging system is used for multiple pulsed source-in-motion X-ray image acquisition of a patient. The acquired images include projection images where each projection image represents an X-ray based forward projection of the acquired images from a specific acquisition angle. A virtual phantom is generated by using the projection images as training data set to develop X-ray image knowledge and image recognition neural network model. The developed image recognition neural network model can be used to reconstruct tomosynthesis images optionally. An artificial intelligence software package receives the generated tomosynthesis images and acquires updated X-ray image knowledge to generate further updated tomosynthesis images optionally. The generated tomosynthesis images are transmitted to the artificial intelligence software package to update the image recognition neural network model using the image recognition neural network model and or the artificial intelligence software package. an X-ray technician can select appropriate acquisition angles to provide a chosen tomosynthesis image of the patient that indicates a clinically standard view of the patient.

With the validated training data, the AI system can be trained. During operation, patient data are input to a radiography X-ray acquisition system. The system is configured to acquire at least one X-ray image from a patient in at least one projection plane. Wherein the X-ray image is at least one of forward projected and or backward projected and or reconstructed from at least one image volume acquired by an X-ray imaging device. A tomosynthesis image reconstruction module is configured to reconstruct an X-ray image of an organ or other tissue from the at least one X-ray image of the patient. An X-ray image analysis module is configured to determine a distribution of nodules in the lung or other tissue. An artificial intelligence module is configured to create X-ray image knowledge based on the determined distribution of nodules. A software package running on a computer system includes an artificial intelligence AI training network that is configured to receive X-ray training images and to develop X-ray image knowledge based on the received X-ray training image. The software package also includes an X-ray image recognition software package. The X-ray image recognition software package is configured to receive the X-ray image knowledge receive the acquired X-ray images from the X-ray imaging device and based on the X-ray image knowledge determine whether the clinically standard views indicate normal function.

The resulting system can be used to speed up diagnosis. When capturing lung cancer screening X-ray images, a radiation technician conventionally acquires images that show the entirety of a patient's left lung, for example. A radiologist will then review the X-ray images and if necessary have the X-ray technician develop additional X-ray images that show the whole of the patient's right lung. Since this process is time consuming, it can add to a significant delay in diagnosing lung cancer. An appropriate combination of X-ray images will indicate which portions of the patient's lungs are clear and free of any abnormalities such as nodules. The AI system trained with anthropomorphic chest phantoms also known as synthetic phantoms using the processes described above can improve the operation of the diagnostic imaging equipment.

Methods for multiple pulsed source-in-motion tomosynthesis image recognition and learning algorithm are described next. A way for multi pulsed source in motion tomosynthesis image recognition using artificial intelligence includes receiving a plurality of X-ray images from an X-ray imaging device. The plurality of X-ray images are acquired while an X-ray source scans across an object as training data. The system provides training data to a multiple pulsed X-ray source-in-motion tomosynthesis image recognition system. Using artificial intelligence as a diagnostics tool for multiple pulsed X-ray source-in-motion tomosynthesis imaging system uses artificial intelligence (AI) to capture tomosynthesis images as much as possible and send them to AI module, which applies various algorithms such as single nodule detector, tumor cluster detection, and reject false detections, for example.

It can be seen from the above description that the embodiments of the present invention use multiple pulsed X-ray sources-in-motion tomosynthesis imaging systems 1, and artificial intelligence training networks for X-ray image recognition methods. The process is composed of two parts. One is to develop X-ray image knowledge based on the X-ray training images, the other, is to create such updated X-ray image knowledge by continuing the process of recognizing new and acquired X-ray images through updates to the X-ray image knowledge developed using the previous X-ray training images. By creating a reliable X-ray image knowledge base, the method can further increase the efficiency of subsequent diagnostics processes. Furthermore, the developed X-ray image knowledge is continuously updated as more X-ray images are received and can therefore adapt to changes in anatomy and physiology.

Although the invention is described above in terms of various exemplary embodiments and implementations, it should be understood that the various features, aspects, and functionality described in one or more of the individual embodiments are not limited in their applicability to the particular embodiment with which they are describe. But instead may be applied alone, or in various combinations, to one or more of the other embodiments of the invention. Whether or not such embodiments are described and whether or not such features are presented as being a part of an illustrated embodiment. Thus the breadth and scope of the present invention should not be limited by any of the above-described exemplary embodiments.

What is claimed is:

1. An apparatus, comprising:
    a set of multiple pulsed X-ray source-in-motion tomosynthesis imaging system to acquire X-ray images of a human patient or an object for artificial intelligence training; and
    an X-ray image recognition software package configured to:
    receive the acquired X-ray tomosynthesis images;
    automatically determine whether the received X-ray images indicate a nodule or lesion in a human body or a flaw in an object.

2. The apparatus of claim 1, wherein the artificial intelligence training includes implementing at least one of a deep learning network or a convolutional neural network.

3. The apparatus of claim 1, the X-ray imaging system includes a user interface (GUI) operable to receive a selection of a plurality of X-ray tomosynthesis images with clinically standard views.

4. The apparatus of claim 1, wherein the X-ray image recognition software package is operable to automatically determine whether the received X-ray tomosynthesis images indicate a nodule or lesion condition.

5. The apparatus of claim 1, wherein the X-ray image recognition software package is further configured to indicate a nodule or lesion condition.

6. The apparatus of claim 1, comprising:
    a primary motor stage moving freely on an arc rail with a predetermined shape;
    a primary motor that engages with said primary motor stage and controls a speed of the primary motor stage;
    a plurality of X-ray sources each mounted at the primary motor stage;
    a supporting frame structure that provides housing for the primary motor stage; and
    an X-ray flat panel detector to receive X-ray and transmit X-ray imaging data.

7. The apparatus of claim 1, wherein the imaging system performs one or more of the following:
    selecting a set of acquired CT chest 3D image data from real patients with known nodules for artificial intelligence training;
    generating synthetic tomosynthesis raw image data using CT forward projection data with multiple pulsed X-ray source-in-motion tomosynthesis imaging system;
    generating synthetic tomosynthesis images from raw image data using backward projection reconstruction;
    transmitting to image recognition software package as image input;
    determining whether chest images indicate a nodule or lesion condition based on X-ray image knowledge; and
    storing output X-ray images to knowledge data base.

8. The apparatus of claim 1, wherein the imaging system performs one or more of the following:
    scanning an object with an X-ray full view using multiple X-ray source-in-motion tomosynthesis imaging system;
    locating region of interest using artificial intelligence after an initial scan.

* * * * *